(12) United States Patent
Vollmann et al.

(10) Patent No.: US 7,980,426 B2
(45) Date of Patent: Jul. 19, 2011

(54) DEVICE FOR DOSED DISCHARGE OF A POWDER-FORM MEDIUM

(75) Inventors: Markus Vollmann, Gelnhausen (DE); Wolfgang Lehnhoff, Bad Homburg (DE); Carsten Weisner, Friedberg (DE); Peter Kreuder, Bad Nauheim (DE)

(73) Assignee: Degudent GmbH, Hanau (DE)

( * ) Notice: Subject to any disclaimer, the term of this patent is extended or adjusted under 35 U.S.C. 154(b) by 863 days.

(21) Appl. No.: 11/956,668

(22) Filed: Dec. 14, 2007

(65) Prior Publication Data

US 2008/0156832 A1    Jul. 3, 2008

(30) Foreign Application Priority Data

Dec. 27, 2006  (DE) .................. 10 2006 062 304

(51) Int. Cl.
    *G01F 11/10* (2006.01)
(52) U.S. Cl. ..................................... 222/361; 222/145.1
(58) Field of Classification Search .......... 222/361–364, 222/145.1, 344–355
    See application file for complete search history.

(56) References Cited

U.S. PATENT DOCUMENTS

| | | | |
|---|---|---|---|
| 2,375,252 A | | 5/1945 | Sayre |
| 4,964,546 A | * | 10/1990 | Morrow et al. ............... 222/352 |
| 5,421,491 A | * | 6/1995 | Tuvim et al. .................. 222/336 |
| 5,855,300 A | * | 1/1999 | Malki ....................... 222/153.09 |
| 6,450,371 B1 | * | 9/2002 | Sherman et al. ............... 222/361 |
| 6,749,091 B2 | * | 6/2004 | Connelly et al. ............... 222/361 |
| 6,929,158 B2 | * | 8/2005 | Smiley .......................... 222/366 |
| 6,962,274 B1 | * | 11/2005 | Sherman ....................... 222/361 |
| 7,472,810 B2 | * | 1/2009 | Amir .............................. 222/361 |
| 2004/0173643 A1 | | 9/2004 | Tuvim |
| 2005/0252456 A1 | * | 11/2005 | Allis ........................... 119/51.04 |
| 2006/0265821 A1 | * | 11/2006 | Hause ............................ 15/22.1 |

FOREIGN PATENT DOCUMENTS

| | | |
|---|---|---|
| DE | 137635 | 2/1902 |
| DE | 7902889 | 5/1979 |
| DE | 3336274 | 4/1985 |
| DE | 3422486 | 5/1985 |
| DE | 10023971 | 7/2001 |
| EP | 0079239 | 5/1983 |
| WO | 2005108934 | 11/2005 |

\* cited by examiner

*Primary Examiner* — Lien T Ngo
(74) *Attorney, Agent, or Firm* — Dennison, Schultz & MacDonald

(57) ABSTRACT

A device (10) for the dosed discharge of a powder-form medium, in particular ceramic powder for dental purposes, including a storage container (12) with a first outlet (40), as well as a slider (20) with a receptacle (18) for a quantity of medium to be dosed, which can be selectively aligned with a first outlet or a second outlet (50), through which the medium can be discharged. In order to achieve reproducible discharge of a defined quantity of free-flowing medium in an uncomplicated design, and since there is no requirement for re-usability after emptying the storage container, the invention proposes that the slider (20) be connected to at least one spring element (26, 28), which admits a force upon the slider to align the receptacle (80) with the first receptacle (40), and that the receptacle can be secured by a lock element (34) in a position aligned with the second outlet (50).

32 Claims, 7 Drawing Sheets

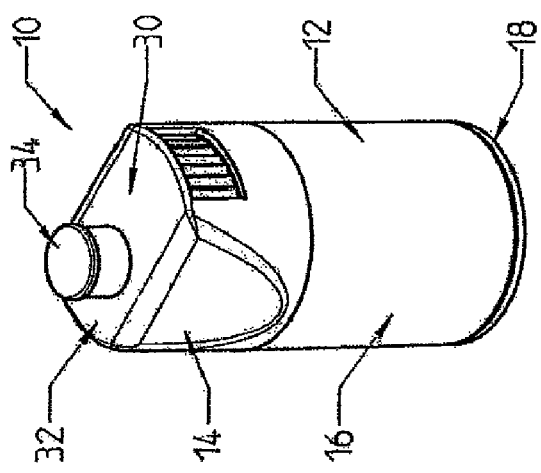
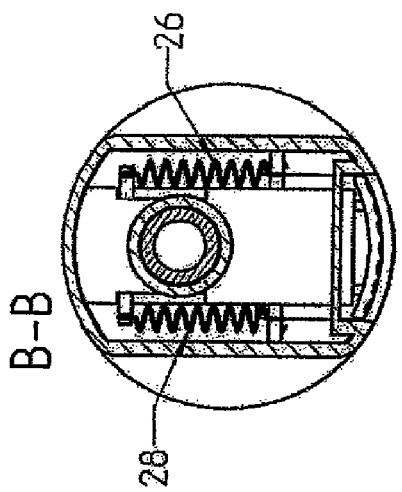
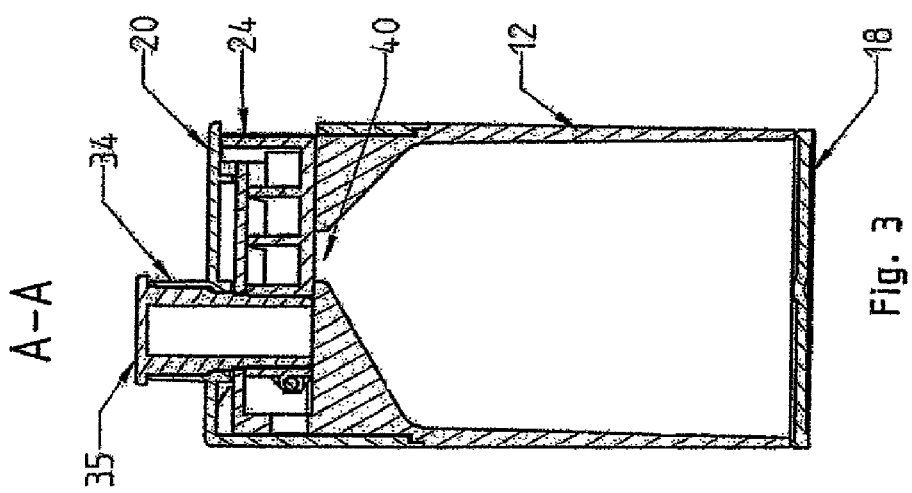
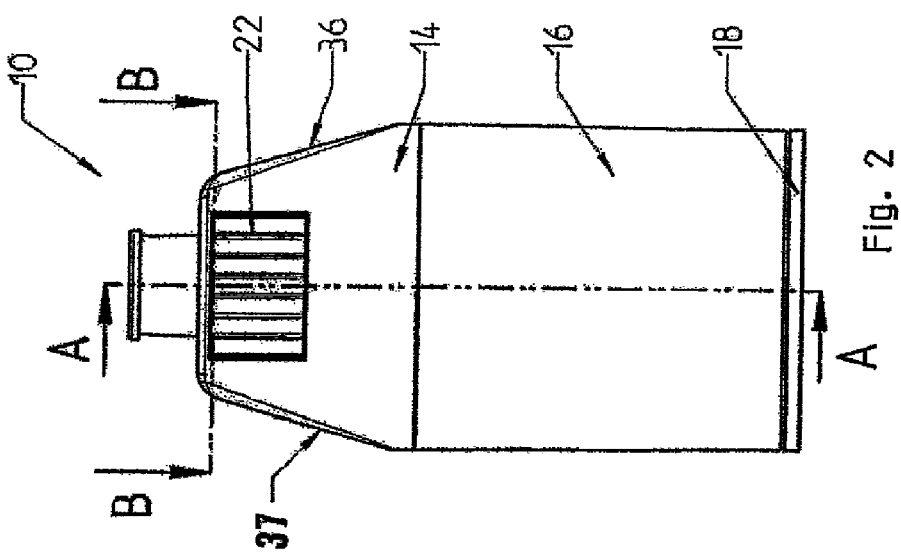

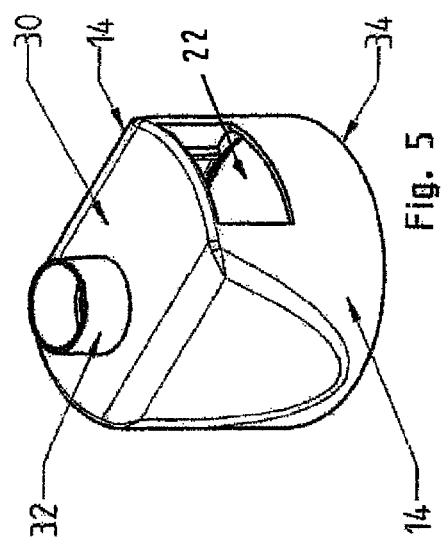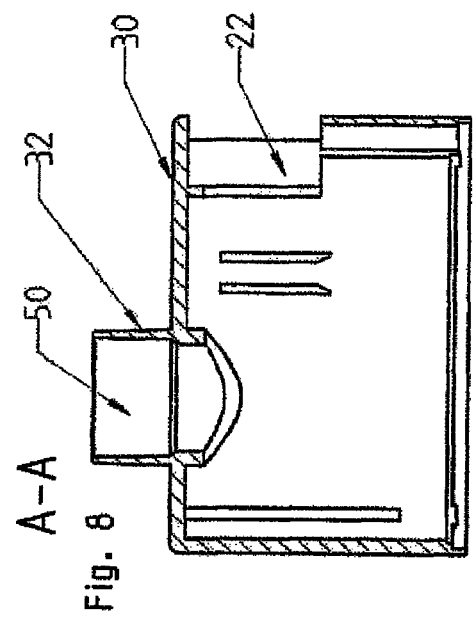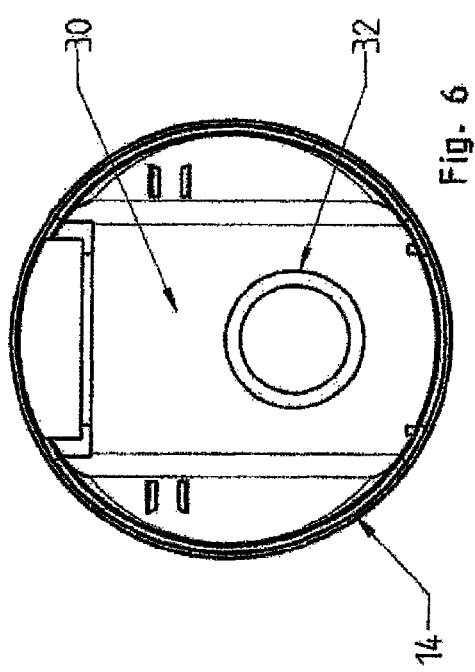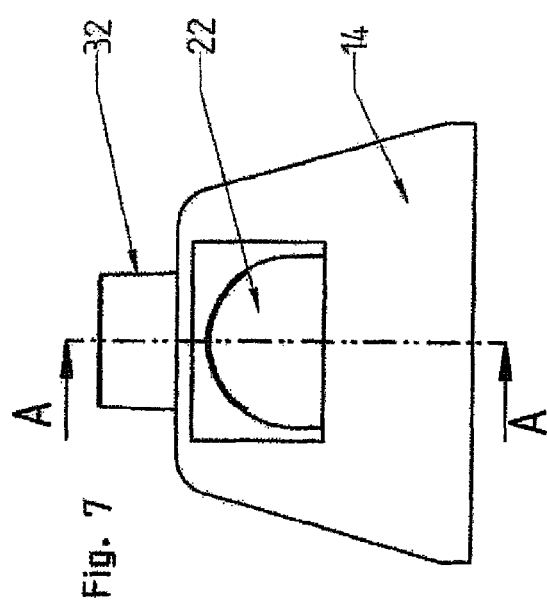

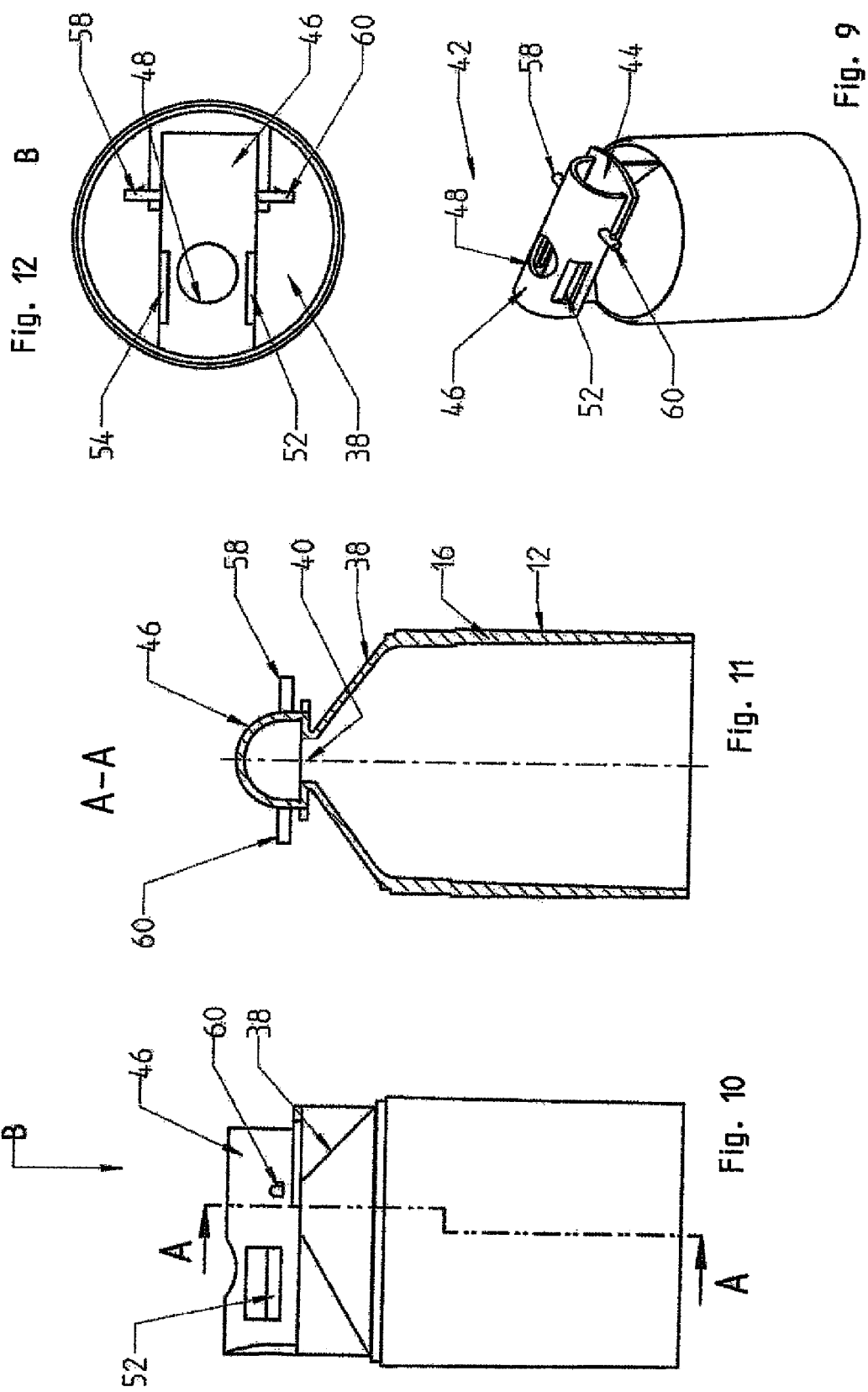

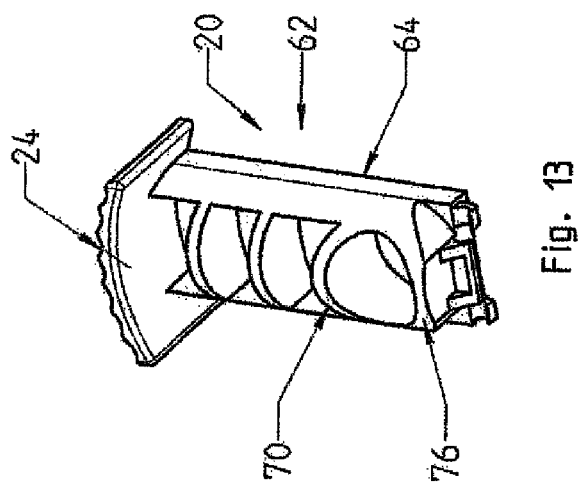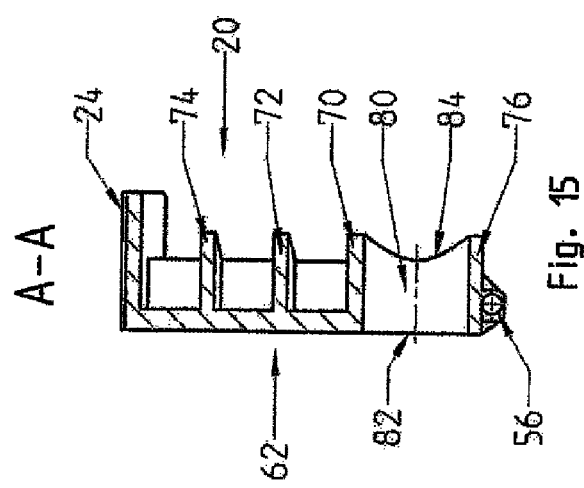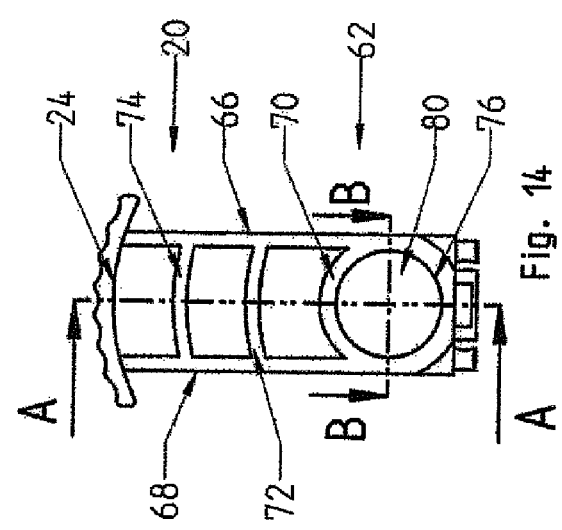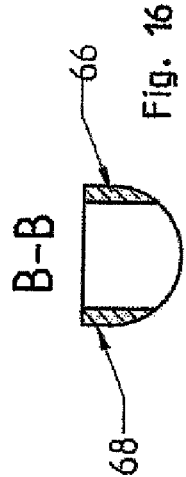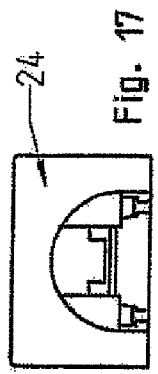

DEVICE FOR DOSED DISCHARGE OF A POWDER-FORM MEDIUM

BACKGROUND OF THE INVENTION

The invention relates to a device for dosed discharge of a powder-form medium, in particular ceramic powder for dental purposes, comprising a housing—providing a storage container—with a first outlet, a cover—extending from or connected to the housing—with a second outlet for delivering the medium, as well as a slider, which can be shifted within the cover to selectively align with either the first or the second outlet, with a receptacle for a quantity of medium to be dosed, whereby the slider interacts with at least one spring element, via which a continuous force is applied to the slider to align the receptacle with the first outlet.

Dosing devices of a corresponding type are employed in various branches of industry to deliver a predetermined quantity of a medium, e.g. to a subsequent manufacturing process.

DE-C-33 36 274 describes a container lid that can be screwed onto a glass vessel or tin can to be able to discharge in a dosed manner consumable goods such as coffee or tee. The lid comprises a slider that features a receptacle for the dosed discharge of the consumable goods. Via arms issuing from the slider, the slider is hinged to pins issuing from the lid. The arms, which exhibit the effect of spring elements, cause the slider to be positioned selectively in a first or a second position, as long as no external forces are applied.

A dosing apparatus for e.g. sugar is described in DE-A-34 22 486. A dosed quantity can be accommodated by a receptacle of a slider, which is acted upon by a force of a spring in such a manner that the receptacle is aligned with a discharge opening, which opens into the dosing device's reservoir holding the sugar.

In a device for portioned discharge of for example coffee or tea, a cover comprises a slider, which by means of integrally moulded spring leafs—together with a dosing chamber receiving the medium to be dosed—is always aligned with an opening that is connected to the reservoir for the medium (DE-A-100 23 971).

A box for powder-form goods such as snuff tobacco is described in DE-U-79 02 889. In this, snuff tobacco is retrieved from a reservoir by means of a slider comprising a dosing chamber. In this, the slider can interact with a spring, so that a force acts upon the dosing chamber in the direction towards the opening of the box.

Subject matter of DE-C-137 635 is a container for automatic discharge of a powder-form or granular medium. For this, a slider is connected to a spring for the purpose of moving the slider together with a dosing chamber towards an opening of a reservoir, from which the medium is to be charged.

EP-A-0 079 239 relates to a dosing apparatus, onto which a container can be screwed. The dosing device comprises a slider that by means of spring elements is held in a position, in which a dosing chamber of the slider is aligned with an opening leading to the container.

Described in DE-A-40 38 274 is a mechanized or automated dosing device, which according to one embodiment comprises a funnel as reservoir with an outlet that is connected to a cylinder, in which a piston that borders an annular space is movable by means of a toothed rack. In this, the space bordered by the piston can be connected either to the outlet extending from the funnel or to a further outlet, to be able to discharge the quantity charged into the space.

In a dosing device according to DE-B-22 28 548, a reservoir is associated with a metering shaft, which comprises a dosing chamber that can selectively be aligned with the reservoir or—after turning the metering shaft—with a delivery opening.

Another option of discharging a dosed quantity of a powder-form material is offered by DE-A-197 27 340. In this, the material is pressed in a cartridge, so that when the cartridge is rotated material can be taken off by means of a stationary knife.

SUMMARY OF THE INVENTION

The present invention is based on the objective to further develop a device of the type mentioned above so that with a simple design a defined quantity of the free-flowing medium can be discharged in a reproducible manner. In this it must be ensured that material can not accumulate and consequently adhere in the receptacle forming a dosing chamber, to rule out the possibility that the quantity to be discharged is inadvertently reduced after several uses. Also, the formation of bridges of material in the housing itself should be prevented. Further, it should be possible to completely empty the housing. At the same time, the device should be cheap to produce, so that re-usability after emptying of the reservoir is not absolutely necessary.

As a solution to this objective, the invention firstly intends that essentially the slider be securable by means of a lock element in a position aligned with the second outlet.

In accordance with the invention, when the device is not being used, the slider will be locked in a position in which the interconnection to the interior of the reservoir is blocked, so that consequently no residuals of the powder-form material to be dosed can accumulate and possibly adhere during further use, which would inadvertently reduce the quantity to be discharged.

To discharge the medium, the lock element is removed and the device is turned by hand to fill the receptacle, i.e. the dosing chamber present in the slider, to feed the powder-form material into the receptacle. Subsequently the slider is moved to the second outlet, which on the one hand interrupts the interconnection to the reservoir, and on the other allows discharge of the quantity of powder-form medium present in the receptacle.

In a solution with its own inventive merit it is intended that the housing contain or be connected to an oscillating device, which can be activated in dependence on the orientation of the housing. The oscillating device can in particular be an unbalanced motor, which ensures that the required amount of medium to be discharged is charged to the receptacle via the first outlet, i.e. in particular when the device is turned in such a manner that its cover is positioned below. The oscillating device is activated only in this position. For this it is particularly intended that an electric circuit containing the oscillating device is closed when the device has been turned for discharging the medium, whereby a switch, e.g. in form of a reed contact that can be actuated via a magnet, is provided to close the electric circuit. The magnet can be supported moveable along the longitudinal direction of the housing and approaches the reed contact to switch the latter, i.e. to close the circuit, when the housing is turned into the discharge position.

In particular, a preferably cylindrical magnet can be arranged moveable in a hollow cylindrical receptacle extending along the longitudinal direction of the housing, whereby the length of the receptacle is greater than the extent of the magnet along the longitudinal direction of the housing. Relative to the switch such as reed contact, the magnet is arranged in such a manner that when the device is not in use, i.e. has been put down, the magnet will be positioned below the switch and in this position will be at a greater distance from the switch than when the housing has been turned by 180° into the position, in which the powder-form or free-flowing medium is being discharged.

In order to secure the magnet e.g. during transport in a position that precludes actuating the reed contact and thus closing the electric circuit, a further development of the invention intends that the receptacle accommodating the magnet, which can also be referred to as a pipe, extends from the bottom wall of the housing component that accepts the reed contact, the unbalanced motor, and the electrical circuitry including battery. In the bottom wall—in extension of the receptacle—is located a position lock such as a cavity, into which a metal part such as a small steel plate, e.g. in form of a plain washer, can be placed, which will keep the magnet in a position along the bottom wall. As a result of this, the distance between the reed contact and the magnet will be too great for the reed contact to be actuated and the electric circuit for the unbalanced motor to be closed. These measures in a simple way provide a shipping brace. Using the dosing device only requires removing the metal part, so that the magnet becomes moveable by gravity to the desired degree within the receptacle, i.e. in particular within the plastic pipe, with the result being that when the top component of the housing, i.e. the second outlet, points downward, the magnet slides in the direction towards the reed contact, actuates the latter, and the unbalanced motor will be activated as a result.

In particular, the device features a cylindrical housing as storage container, which can be closed by a cap-like cover such as a hood, in which the slider is movably supported under the effect of a spring force. Along the circumferential wall side, the cover should at least in some sections be flush aligned with the outer surface of the housing. The cover features an opening as first opening, into which the slider is moveable into the cover against a force generated by the spring element to shift alignment from the first outlet to the second outlet. Further, the cover should be flat-topped on the top side and should feature a surface, which extends perpendicular to the longitudinal axis of the housing and through which passes the second outlet, which preferably is encompassed by a hollow cylindrical projecting part projecting from the surface. Inserted into the hollow cylindrical projecting part can be a cylindrical body forming the lock element, which secures the slider when the receptacle is aligned with the second outlet. In this position the slider blocks the first outlet.

To ensure a controlled adjustment of the slider, the slider is accommodated in a guide way extending in the cover perpendicular to the longitudinal axis of the housing.

The housing itself, which is closed by the cover, should on the cover side feature a cap-like, e.g. cone- or truncated-cone-shaped, extension that borders the first outlet, whereby the guide way for the slider extends from this extension itself. In this, the guide way can consist of a plate-shaped base element with a flat geometry on the slider side and, extending from this base element, a curved element with an inside geometry that is matched to the outside geometry of the slider.

The base element features an opening as second opening, which connects to the first outlet, whereby along the longitudinal direction of the base element, offset relative to the second opening, the curved element is intersected by an opening as third opening, which connects to the second outlet.

The slider is moveable within the guide way and is acted upon by means of a spring element in such a way that the receptacle has the tendency to be aligned with the first outlet. For the purpose of fixing the spring element with simple means and to let the required force become effective, it is intended that from a first end region of the guide way, in particular from the curved element, which features the cross section of a segment of a circle such as semi-circle, extend a first mounting element, which in particular is formed by pin-shaped projections projecting from the respective longitudinal edge region of the guide way. As opposite mounting element for the spring element, a pin-shaped element should issue from the slider, extend on both sides of the guide way, and pass through corresponding longitudinal slits in the guide way. This creates the possibility of positioning a spring element such as a tension spring on each longitudinal edge of the guide way, to exert a force upon the slider.

Along its circumferential side, the slider should exhibit a semi-cylindrical geometry, the flat side of which, forming the bottom wall, rests upon the base element and is movable along the latter.

Extending from the bottom wall of the slider are preferably ridge-shaped walls, which extend perpendicular to the longitudinal axis of the slider and border the receptacle, i.e. the dosing chamber. Correspondingly, the bottom wall features an opening as fourth opening, which can be aligned with the first outlet. On the circumferential side, the border walls are matched to the interior circumferential geometry of the curved element, forming a receptacle closed along the circumferential side into which the quantity to be dosed can be fed in the form of a powder-form medium. Relative to the fourth opening, the receptacle is not covered by the slider and, in dependence on the position of the slider, the receptacle will be blocked by the guide way or will be connected via the third opening to the second outlet.

To facilitate its operation, the slider exhibits in its region facing the first opening a preferably textured boundary wall to be used as handle. When the slider is not engaged to the lock element, the boundary wall for shifting the slider extends outside the cover.

Further, the slider can comprise several stiffening ribs, which extend from the bottom wall and on the circumferential side are in at least sections matched to the inner circumference geometry of the curved element of the guide way.

As mentioned above, the lock element should have a cylindrical shape, whereby a stepped geometry is preferred that matches the inner geometry of the regions of the cover or guide way, into which the lock element engages. Independent thereof, the lock element should feature on its end a cover element that is embodied flange-like and along its circumference side is aligned flush with the circumferential surface of the hollow cylindrical projection of the cover or possible protrudes laterally, when the lock element has been engaged, to facilitate an easy hand-hold for removal from the hollow cylindrical projecting part.

The cover can be material-bonded to the housing in particular by ultrasonic welding. The bottom wall of the housing as well should be welded by ultrasound to the circumferential wall. Other material-bonding processes such as gluing are also feasible.

BRIEF DESCRIPTION OF THE DRAWINGS

Further details, advantages and features of the invention are not only found in the claims, the characteristic features described therein—on their own and/or in combination—but also in the following description of a preferred embodiment example illustrated in the drawings.

FIG. 1 shows a perspective view of a dosing device.
FIG. 2 shows a front view of the dosing device of FIG. 1.
FIG. 3 shows a section along the line A-A in FIG. 2.

FIG. 4 shows a section along the line B-B.

FIG. 5 shows a perspective view of a hood covering the device of FIG. 1.

FIG. 6 shows a magnified top view of the hood of FIG. 5.

FIG. 7 shows a front view of the hood of FIG. 5.

FIG. 8 shows a section along the line A-A in FIG. 7.

FIG. 9 illustrates the housing of the device of FIG. 1.

FIG. 10 shows a sectional view of the housing of FIG. 9.

FIG. 11 shows a section along the line A-A in FIG. 10.

FIG. 12 shows a view along the direction B of FIG. 10.

FIG. 13 shows a perspective view of a slider of the device of FIG. 1.

FIG. 14 shows a top view of the slider of FIG. 13.

FIG. 15 shows a section along the line A-A in FIG. 14,

FIG. 16 shows a section along the line B-B in FIG. 14,

FIG. 17 shows a rear view of the slider of FIG. 13.

DESCRIPTION OF THE PREFERRED EMBODIMENTS

Figure 18:
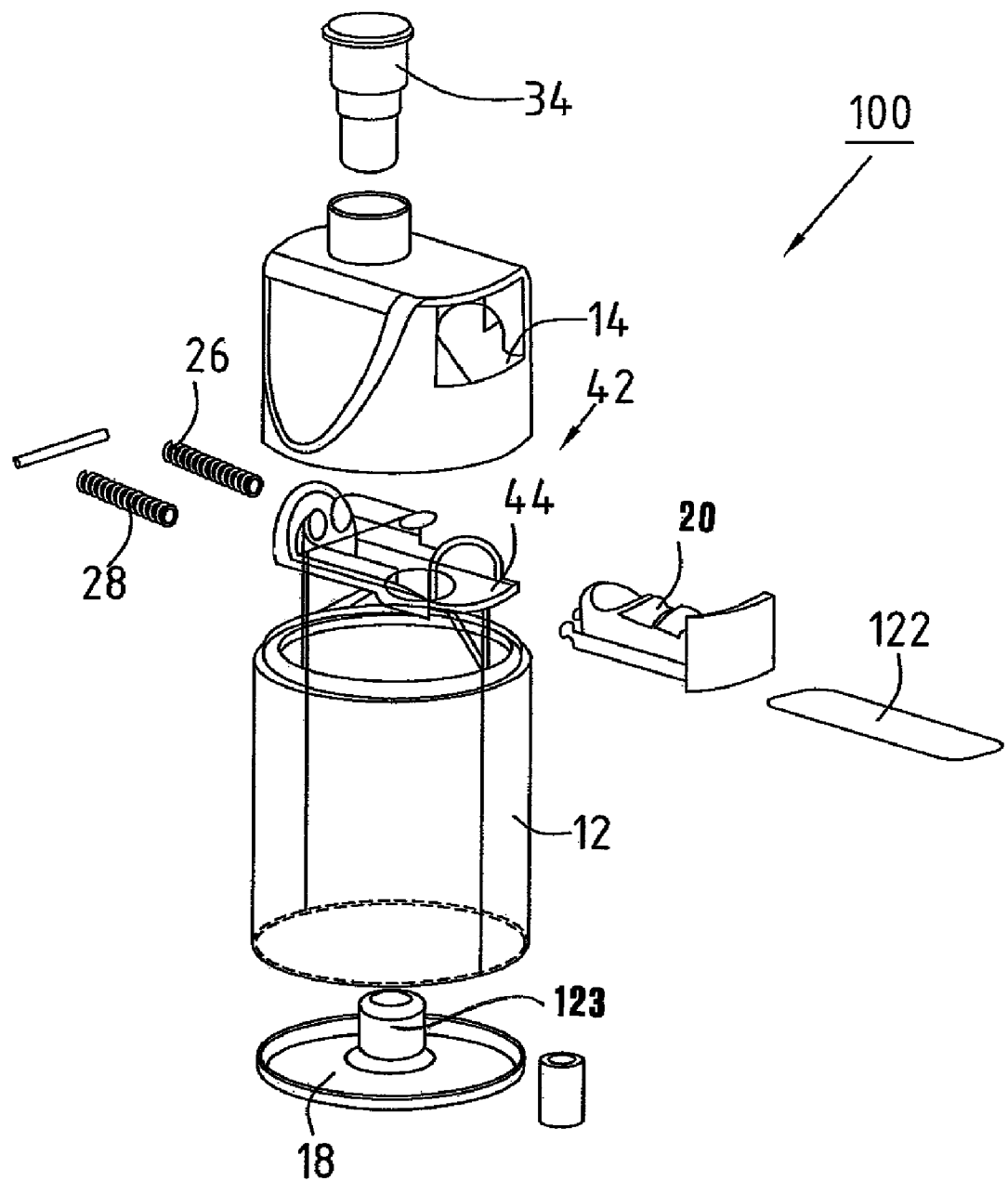
FIG. 18 shows an exploded view of a further embodiment of a dosing device.

FIGS. 1 to 17 illustrate elements and details of a dosing device 10, which can be used to discharge a defined quantity of free-flowing media, in particular powder-form material such as ceramic powder for the dental field. However, the cases of application given as examples in this regard should not be understood as limiting the scope of protection, even though they are preferred.

The device 10 comprises a housing 12, which is closed on its topside by a cover that will be referred to as hood 14 hereinafter. The hood 14 can be material-bonded to the housing 12 by means of ultrasonic welding. The housing 12 comprises a cylindrical-shape main body 16, which is closed on the bottom by a bottom wall 18, which also can be material-bonded to the housing body 16 by means of ultrasonic welding. The free-flowing medium to be discharged in a dosed manner is charged into the housing 12 with its bottom wall 18 removed. Subsequently, the housing 12 is closed by the bottom wall 18. Thus the housing 12 constitutes a storage container.

To be able to reproducibly discharge a dosed quantity of the medium, a dosing device in form of a slider 20 is provided, which will be explained in more detail on the basis of FIGS. 13 to 17 in connection with FIGS. 9 to 12. The slider 20 is movable in the hood 14 perpendicularly to the longitudinal axis of the housing 12. For this purpose, the hood 14 features a cut-out as an opening 22, which can engage a front wall 24 of the slider 20, to be pushed into the hood 14 against the force of tension springs 26, 28.

On its top, the hood 14 features a flattened region 30, from which protrudes a projecting part 32 with a hollow cylinder geometry, into which a cylindrical-shape lock element 34 can be inserted, to position the slider 20 in the position illustrated in FIGS. 1 and 3. The lock element 34 can feature a lid element 35 of a flange-like embodiment to facilitate problem-free handling.

The hood 14 has a cylindrical geometry with two opposite outside surfaces 36, 37 extending at an angle. The surfaces 36, 37 extend alongside the slider 24. In the remaining surfaces, the circumferential surface of the hood 30 approximates sections of a cylinder circumferential wall surface. Furthermore, the outer side of the hood 14 continues with a flush alignment into the outer surface of the main or base body 16 of the housing 12.

The housing 12, i.e. the cylinder-shaped base body 16, at its upper side changes into a head section 38 or extension, which has a truncated-cone geometry and features a funnel shape on the inside. The head section 38 surrounds a first outlet 40. The head section 38 can be a component manufactured separately by e.g. injection moulding and can be material-bonded to the base body 16, e.g. using ultrasonic welding. From the head section 38 extends a guide way 42 for the slider 20. The guide way 42 comprises a plate-shaped base section 44, —also referred to as base element—, which is covered by a pipe-section-shaped element 46 with an arc-shaped cross-section and an inside geometry that matches the effective circumferential geometry of the slider 20. This provides an accurate guide way for the slider 20. The guide way 42 extends perpendicular to the longitudinal axis of the housing 12.

The base section 44 features a cutout, which is to be referred to as second opening and which opens into the first outlet 40.

The curved element 46 features an opening 48 as third opening, which extends flush with the hollow-cylinder-shaped projecting part 32 that surrounds a second outlet 50. A pin element, which can be referred to as axle 56 and which is fixed in the region at the rear side of the slider 20 and extends at a right angle to the latter's two longitudinal sides, passes through longitudinal slits 52, 54, which extend along the base element 44 in the region of the third opening 48.

Pin-shaped projections 58, 60 protrude from the forward region of the curved element 46, in particular in a direction that corresponds to that of the axle 56. The tension springs 26, 28 are mounted in between the laterally protruding sections of the axle 56 and the projections 58, 60, as a result of which the slider 20 is acted upon by a force in the direction toward the front end of the guide way 42 and thus the opening 22 in the hood 14.

The slider 20 has a base body 62, which comprises a base plate 64 and—extending from the latter—ridge-shaped longitudinal-side-wall sections 66, 68. In between the latter extend boundary walls 70, 72, 74. The front boundary walls 72, 74 represent rib-like reinforcements. In contrast, a rear partition wall 70 together with a rear boundary wall 76 of the slider surround a receptacle 80, into which can flow the medium to be transferred from the housing 12. The receptacle 80 is open at its lower side, and consequently has an opening (fourth opening) 82. This opening 82 can be aligned with the second opening (not illustrated) of the plate-shaped base section 44 of the guide way 42, which in turn connects to the first outlet 40. The receptacle 80 and thus its opening 82 is aligned with the first outlet 40 when the slider 20 is exclusively acted upon by the forces exerted by the tension springs 26, 28. In this case, the forward textured front or boundary wall 24 of the slider 20 is located outside the hood 14. In this position, the receptacle 80 is accessible via the opening 82, whereas the remaining region is covered by the guide way 42, i.e. the curved element 46. For filling the receptacle 80 in this position of the slider 20, the dosing device 10 must be rotated by approximately 180°. Subsequently the slider 20 is pushed into the hood 14 against the force of the springs 26, 28. This closes the opening 82 of the receptacle 80. When the slider 20 has been pushed into the hood 14—this movement is restricted by the interaction between the axle 56 and the limits of the slits 52, 54—the receptacle 80 with its upper opening 84 located opposite its bottom wall opening reaches true alignment with the third opening 48 and thus the second outlet 50, so that the medium contained in the receptacle 80 can be discharged.

Subsequently, the lock element 34 can be inserted via the second opening 50 so that it penetrates all the way to the slider 20, i.e. the receptacle 80, in order to arrest the slider 20. In this position the front wall 24 of the slider 20 is approximately aligned with the exterior surface of the hood 14, as is shown schematically in the illustrations of FIGS. 1 to 4.

The invention provides with uncomplicated mechanical measures a dosing device for the dosed discharge of a free-flowing medium, in particular ceramic powder, which can be used as a single-use dosing device. Of course the design is also suitable for repeated use. In this case, the bottom wall 18 would have to close the base body 20 in a detachable manner.

The individual component parts of the device 10 consist of plastic and can be injection-moulded parts. The guide way 42 can as a separate part be joined by ultrasonic welding to the cap-shaped head section 38 of the housing 12. Other fastening methods are also feasible.

Figure 19:
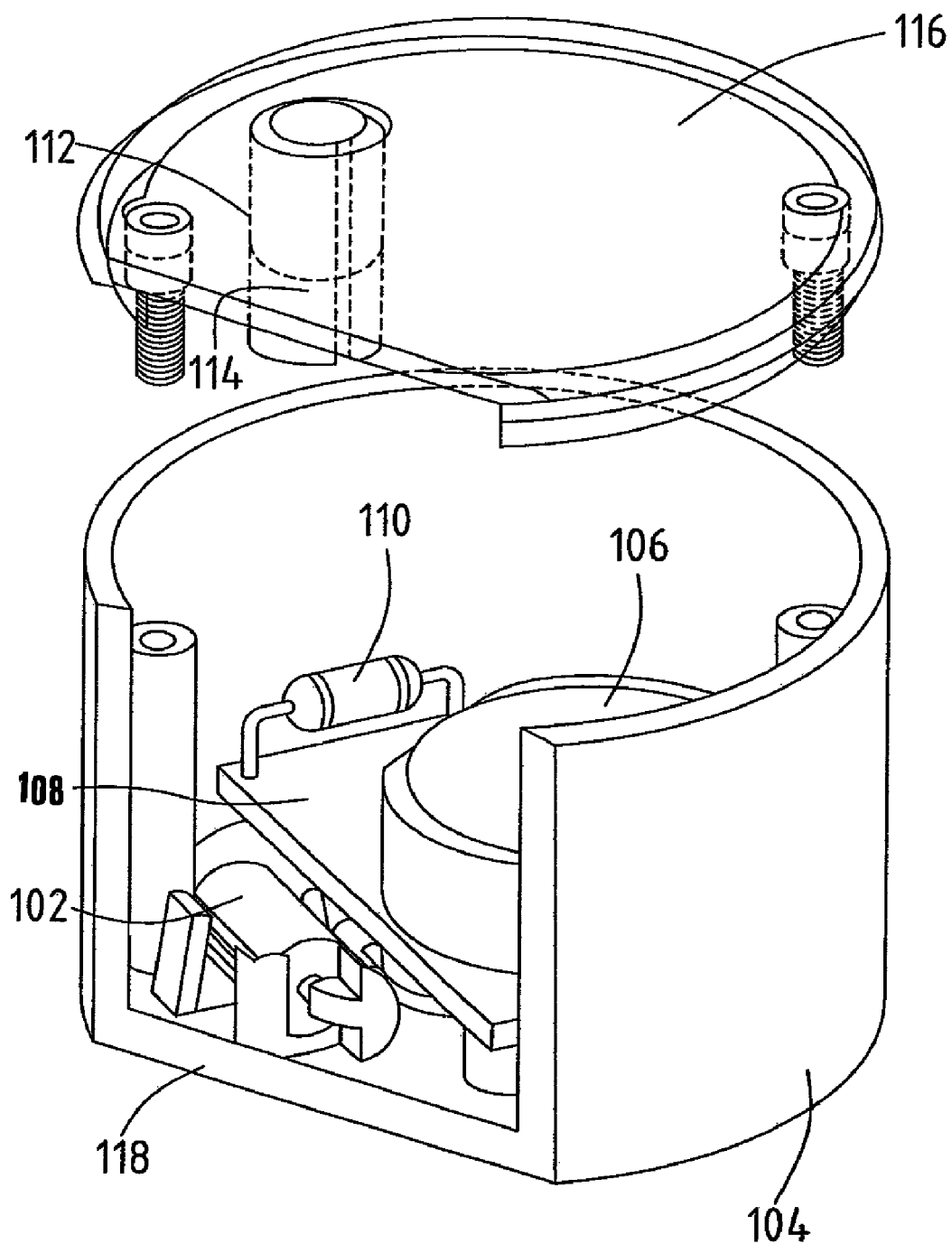
FIG. 19 shows a first perspective view of a part connectable to the device of FIG. 18.
Figure 20:
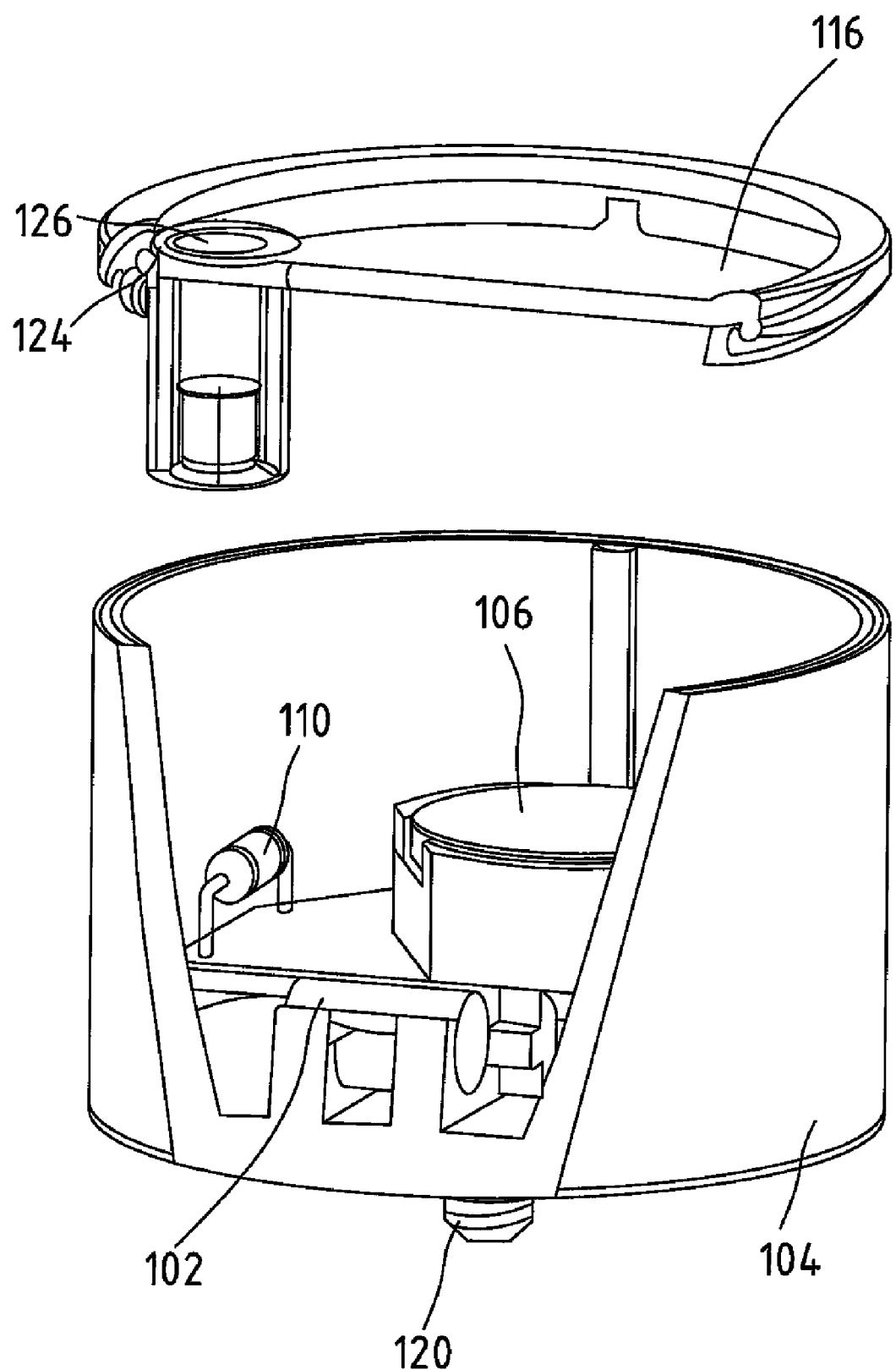
FIG. 20 shows a different perspective view of the part of FIG. 19.

FIGS. 18 to 20 illustrate a further embodiment of the invention's dosing device 100, which in regard to the arrangement of the slider, the housing containing the fluid medium to be discharged, and the cover corresponds to the device of FIGS. 1 to 17, so that identical reference symbols can be used for equivalent elements. In this respect we also refer to the explanations in connection with FIGS. 1 to 17.

Divergent from the embodiment example explained above and supplementary to it, the device 100 comprises an oscillating device 102, which preferably is embodied as an unbalanced motor. The oscillating device 102, which in the following will be referred to as unbalanced motor for simplicity, is activated when medium is to be discharged. In this, the unbalanced motor serves to ensure that the required amount of free-flowing material can flow via the first outlet 40 into the receptacle 80, i.e. the dosing chamber in the slider 20, so that it can be discharged after aligning the receptacle 20 with the second outlet. Thus the unbalanced motor 102 ensures the consistent discharge of medium from the housing 12. At the same time it is ensured that no material or powder residue remains in the housing 12, which allows optimal utilization.

In accordance with the embodiment example of FIGS. 19 to 20, the unbalanced motor 102 is located in a housing section 104, which preferably can be screw-mounted to the housing 12 and which together with the bottom 18 of the housing 12 forms a quasi double bottom. The housing section 104 houses a circuit board 108 for the electrical wiring of the unbalanced motor 112. The drawing illustrates a battery such as a button cell 106, which is connected to the unbalanced motor 102, in particular via the circuit board 108. For opening and closing the electric circuit, a reed contact 110 is provided, which is actuated via a magnet 112, which is arranged moveable along the longitudinal direction of the housing 12 in a receptacle 114.

The receptacle 114 extends from the bottom wall 116 of the housing section 104, so that when the device 100 has been put down or is held in a position in which the cover 14 is facing upward, the magnet 112 will be sufficiently distant from the reed contact 110 for the latter not to close, with the result that the electric circuit for the unbalanced motor 102 is interrupted. When the device 110 is rotated, i.e. to discharge free-flowing medium, the magnet 112 moves in the receptacle 114 forming a guide way in the direction towards the reed contact 110, so that the latter is closed and the unbalanced motor 102 is activated. The vibration generated by the unbalanced motor 102 causes the free-flowing or powder-form material present in the housing 12 to be conveyed in the direction towards the first outlet 40, to reproducibly fill the receptacle 80 in the slider 20.

In its boundary wall 118 that is located opposite its bottom wall 116, the housing section 104 features a metal insert part 120, which has a screw thread and can be screwed into a threaded bush 123, which extends from or passes through the bottom wall 18 of the housing 12.

FIG. 18 further illustrates that the base element 44 of the guide way 42 for the slider 20 can be covered by foil 122, which is to be removed prior to the first use of the device 10/100. This ensures that the interior of the housing 12, i.e. the storage reservoir, is sealed airtight during transport and storage, providing protection against ingress of humidity.

As illustrated in FIG. 20, the receptacle 114—which consists of plastic—has the shape of a pipe that extends from the interior side of the bottom wall 116 of the second housing 104. On the outside and in extension of the receptacle 114, the bottom wall 116 features a receiver such as a cavity 124, into which a metal part such as a small steel plate or plain washer 126 can be inserted and wedged, which holds the magnet 112 in a position in the region of the bottom wall 116, i.e. in the part of the pipe or receptacle 114 that extends from the interior side of the bottom wall 116. As a result, the magnet 112 will be at a sufficiently large distance from the reed contact 110, so that the latter will not be actuated, and the circuit that includes the unbalanced motor 112 will not be closed. This provides a simple shipping brace. When the dosing device 10 is to be operated it is only necessary to remove the metal part 126 from the receiver 124 located in the bottom wall 116, so that the magnet 112 can be moved by gravity within the receptacle 114. Consequently, the reed contact 110 is actuated and thus the circuit that contains the unbalanced motor 102 is closed, if the dosing device 10 is rotated in such a manner that its head, i.e. the second outlet 50, points downward. Consequently, activation of the unbalanced motor 102 causes the powder-form medium present in the housing 12 to vibrate, giving rise to flowability, so that the required volume of powder material can flow into the receptacle 80 of the slider 20 that constitutes a dosing chamber.

REFERENCE LIST

10 Dosing device
12 Housing
14 Cover/Hood
16 Main body
18 Bottom wall
20 Slider
22 First opening
24 Front wall
26 Tension springs
28 Tension springs
30 Flattened region
32 Projecting part
34 Lock element
35 Cover element
36 Side surface
37 Side surface
38 Head section
40 First outlet
42 Guide way
44 Base section
46 Element
48 Third outlet
50 Second outlet
52 Longitudinal slit 54 Longitudinal slit
56 Axle
58 Projecting part
60 Projecting part
62 Base body
64 Base plate
66 Longitudinal side wall section
68 Longitudinal side wall section
70 Boundary wall
72 Boundary wall
74 Boundary wall
76 Boundary wall
80 Receptacle
82 Opening
84 Opening
100 Device
102 Oscillating device
104 Housing section
106 Button cell
108 Circuit board
110 Reed contact
112 Magnet
114 Receptacle
116 Bottom wall
118 Boundary wall
120 Metal insert
122 Foil
123 Bush
124 Receiver
126 Small metal plate

What is claimed is:

1. A device for dosed discharge of a powder-form medium, comprising:
   a housing that provides a storage container for the medium and has a first outlet,
   a cover which extends from or is connected to the housing and includes a second outlet for discharging the medium,
   a slider which is moveable within the cover, and which is selectively alignable with the first or the second outlet, and includes a receptacle for a quantity of medium to be dosed, the slider interacting with at least one spring element, which continuously exerts a force upon the slider to align the receptacle with the first outlet, and
   a lock element for securing the slider in a position aligned with the second outlet,
   wherein the housing includes on a cover side a cap-like extension, which has a conical or truncated conical shape and surrounds the first outlet, a guide way for the slider extending from the extension, the guide way extending in the cover perpendicular to the longitudinal axis of the housing,
   wherein the guide way comprises a plate-shape base element which has a flat shape on a side facing the slider, and a curved element which extends from and at least partially covers the base element and has an inner geometry that is matched to an outer geometry of the slider, and
   wherein the base element includes as second opening an opening that connects to the first outlet, and, offset relative to the second opening along a longitudinal direction of the base element, the curved element being passed by an opening as third opening, which connects to the second outlet.

2. The device of claim 1, wherein the cover has a circumferential wall including an opening as first opening, through which the slider can be pushed into the cover against a force exerted by the at least one spring element to shift the receptacle from an alignment with the first outlet to an alignment with the second outlet.

3. The device of claim 1, wherein the cover is flattened on a top side and features a top surface which extends perpendicularly to the longitudinal axis of the housing and through which passes the second outlet.

4. The device of claim 3, wherein from the top surface projects a hollow cylindrical projecting part, which forms or surrounds the second outlet, and into which the lock element can be detachably inserted.

5. The device of claim 1, wherein the housing contains or is connected to an oscillating device which activatable in dependence upon orientation of the housing.

6. The device of claim 1, wherein a first mounting element for the at least one spring element extends from an end region of the guide way.

7. The device of claim 6, wherein the first mounting element is formed by pin-shaped projections extending from respective longitudinal edge region of the guide way.

8. The device of claim 1, wherein in a second end region of the guide way, which is located opposite to the first end region, and along a longitudinal direction extends at least one slit, through which passes a second mounting element, extending from the slider, for the at least one spring element.

9. The device of claim 8, wherein the second mounting element is a pin-like element detachably joined to the slider.

10. The device of claim 9, wherein in each respective longitudinal edge region of the curved element extends a slit, through which passes the pin-shaped element.

11. The device of claim 10, wherein along each longitudinal edge region of the guide way extends a spring element, which is mounted between the first and the second mounting elements.

12. The device of claim 1, wherein the slider has along a circumference side a half-cylinder geometry with a flat side that forms a bottom wall, which rests upon the base element of the guide way.

13. The device of claim 12, wherein longitudinal edges, with ridge-shaped partitioning walls extending therebetween, extend from the bottom wall.

14. The device of claim 12, wherein from the bottom wall extend walls which surround the receptacle and having a free circumference matched to an interior circumference geometry of the curved element of the guide way.

15. The device of claim 1, wherein the receptacle includes on a bottom side a fourth opening, which in dependence on the position of the slider can be aligned with the first outlet or is covered by the base element of the guide way.

16. The device of claim 2, wherein in a region that faces the first opening, the slider includes a boundary wall, upon which a force acting from outside the device can be imparted.

17. The device of claim 16, wherein when the slider is disengaged from the lock element, the boundary wall for moving the slider passes through the first opening and extends outside the cover.

18. The device of claim 12, wherein several partitioning walls extend from the bottom wall of the slider, which along circumferential sides are at least in sections matched to a circumferential geometry of the curved element.

19. The device of claim 1, wherein the lock element has a cylindrical geometry.

20. The device of claim 1, wherein the lock element includes sections with differing diameters.

21. The device of claim 4, wherein the lock element includes at an end thereof a flange-like embodied lid element, which along a circumferential side is flush aligned with a circumferential surface of the hollow cylindrical projecting part or laterally protrudes therebeyond.

22. The device of claim 1, wherein the bottom wall of the housing is material-bonded to the circumferential wall of the housing.

23. The device of claim 1, wherein the cover is material-bonded to the housing.

24. The device of claim 1, wherein at least one of the housing and the cover is an injection-molded plastic component.

25. A device for dosed discharge of a free-flowing powder-form medium, comprising:
- a housing that provides a storage container for the medium and has a first outlet,
- a cover which extends from or is connected to the housing and includes a second outlet for discharging the medium, and
- a slider which is moveable within the cover and which is selectively alignable with the first or the second outlet, and which includes a receptacle for a quantity of medium to be dosed,
- the slider interacting with at least one spring element which continuously exerts a force upon the slider to align the receptacle with the first outlet,
- wherein the housing contains or is connected to an oscillating device, which is activatable in dependence on orientation of the housing.

26. The device of claim 25, wherein the oscillating device is arranged in a double bottom of the housing or in a second housing that is joined to the housing which now constitutes a first housing.

27. The device of claim 25, wherein the oscillating device is an unbalanced motor, which is connected to or disconnected from a voltage source by a switch actuatable in dependence on the orientation of the housing.

28. The device of claim 27, wherein the switch is a reed contact.

29. The device of claim 28, wherein the reed contact is associated with a magnet moveable in a longitudinal direction of the housing.

30. The device of claim 29, wherein the magnet has a cylindrical shape and is moveable in a hollow cylindrical receptacle, which extends along a longitudinal direction of the first housing or a second housing in which the oscillating device is arranged and which is joined to the housing, the receptacle having an inner length that is greater than an extent of the magnet along the longitudinal direction of the housing.

31. The device of claim 26, wherein the second housing includes means for screwing to the bottom wall of the first housing.

32. The device of claim 30, wherein the receptacle for the magnet extends from or borders onto a bottom wall of the second housing, and a securable metal part which holds the magnet in position at a bottom wall side, is detachably arranged on the outside, in or at the bottom wall.

* * * * *